(12) United States Patent
Hanano (10) Patent No.: US 8,459,853 B2
(45) Date of Patent: Jun. 11, 2013

(54) LIGHT SOURCE APPARATUS HAVING LIGHT DISTRIBUTION CORRECTION OPTICAL ELEMENT AND ENDOSCOPE SYSTEM INCLUDING SUCH APPARATUS

(75) Inventor: Kazunari Hanano, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/314,589

(22) Filed: Dec. 8, 2011

(65) Prior Publication Data
US 2012/0163015 A1 Jun. 28, 2012

Related U.S. Application Data

(63) Continuation of application No. PCT/JP2011/061197, filed on May 16, 2011.

(30) Foreign Application Priority Data

Jun. 10, 2010 (JP) ................... 2010-133170

(51) Int. Cl.
*F21V 5/08* (2006.01)
*A61B 1/07* (2006.01)

(52) U.S. Cl.
USPC ........ 362/574; 362/17; 362/268; 362/311.09; 362/331; 362/335

(58) Field of Classification Search
USPC ............... 362/16, 17, 572, 574, 268, 311.01, 362/311.06–311.11, 326, 331, 335, 340
See application file for complete search history.

(56) References Cited

U.S. PATENT DOCUMENTS

| | | | | |
|---|---|---|---|---|
| 4,285,578 A * | 8/1981 | Yamashita et al. | ............ | 359/644 |
| 4,403,837 A * | 9/1983 | Nakahashi | ............ | 359/770 |
| 4,492,440 A * | 1/1985 | Nishioka | ............ | 359/734 |
| 4,666,246 A * | 5/1987 | Nishioka et al. | ............ | 385/117 |
| 4,953,937 A * | 9/1990 | Kikuchi et al. | ............ | 385/33 |
| 5,050,584 A * | 9/1991 | Matsuura | ............ | 600/130 |
| 5,143,435 A * | 9/1992 | Kikuchi | ............ | 362/574 |
| 5,746,494 A * | 5/1998 | Koeda et al. | ............ | 362/560 |
| 5,918,968 A * | 7/1999 | Choi | ............ | 362/268 |
| 5,971,576 A * | 10/1999 | Tomioka et al. | ............ | 362/574 |
| 2007/0103912 A1 | 5/2007 | Namii | | |
| 2010/0194290 A1 | 8/2010 | Hanano | | |

FOREIGN PATENT DOCUMENTS

| | | |
|---|---|---|
| EP | 2 157 356 A1 | 2/2010 |
| JP | 62-150315 | 7/1987 |
| JP | 62150315 A * | 7/1987 |
| JP | 6-41001 U | 5/1994 |
| JP | 10-311944 | 11/1998 |
| JP | 2002-214563 | 7/2002 |
| JP | 2003-331622 | 11/2003 |
| JP | 2007-072339 | 3/2007 |

(Continued)

*Primary Examiner* — Ismael Negron
(74) *Attorney, Agent, or Firm* — Scully, Scott, Murphy & Presser, P.C.

(57) ABSTRACT

A light source apparatus includes: a light source section that emits a luminous flux whose quantity of light is larger in a central region than in a peripheral region; a condensing optical system that condenses an incoming luminous flux; and a light distribution correction optical element arranged between the light source section and the condensing optical section, in which a central portion has a negative power that is more intense than that of a peripheral region.

7 Claims, 7 Drawing Sheets

FOREIGN PATENT DOCUMENTS

| | | |
|---|---|---|
| JP | 2007-089861 | 4/2007 |
| JP | 2007-333856 | 12/2007 |
| JP | 2008-305710 | 12/2008 |
| JP | 2009-011461 | 1/2009 |
| JP | 2009-199750 | 9/2009 |
| WO | WO 2008/149905 A1 | 12/2008 |

* cited by examiner

LIGHT SOURCE APPARATUS HAVING LIGHT DISTRIBUTION CORRECTION OPTICAL ELEMENT AND ENDOSCOPE SYSTEM INCLUDING SUCH APPARATUS

CROSS REFERENCE TO RELATED APPLICATION

This application is a continuation application of PCT/JP2011/061197 filed on May 16, 2011 and claims benefit of Japanese Application No. 2010-133170 filed in Japan on Jun. 10, 2010, the entire contents of which are incorporated herein by this reference.

BACKGROUND OF THE INVENTION

1. Field of the Invention

The present invention relates to a light source apparatus that supplies light to a light guide and an endoscope system including the light source apparatus.

2. Description of the Related Art

In light emitted by a light source apparatus that supplies light to a light guide, a light distribution (angular distribution) characteristic including not only a light intensity distribution characteristic but also an angular distribution characteristic is important. In other words, light source apparatuses are required to have not only a light condensing capability of efficiently connecting light from a light source to a light guide in order to ensure brightness of an endoscopic image, but also a wide light distribution characteristic of maintaining an intensity of a luminous flux having a large incident angle relative to a luminous flux in the vicinity of an optical axis of the luminous flux in order to ensure brightness of an outer peripheral portion of the endoscopic image.

In a light source apparatus for an endoscope, which is required to provide bight light, a discharge lamp such as a xenon lamp or a metal halide lamp is used as a light source lamp. However, in a light source lamp including a discharge lamp that includes an discharge electrode arranged on an optical path, the discharge electrode and a valve that includes the discharge electrode therein block light, resulting in occurrence of what is called a hollow defect in which a central region of an emitted luminous flux is darkened. Meanwhile, a light source lamp including a discharge lamp improved so as to emit brighter light, by means of reduction in diameter of, e.g., a discharge electrode, a valve and an opening of a reflector, emits a luminous flux whose quantity of light is larger in a central region than in a peripheral region.

In Japanese Patent Application Laid-Open Publication No. 2003-331622, the present applicant discloses a light source apparatus including an integrator portion. The integrator portion includes an entrance-side integrator lens, an exit-side integrator lens and a condensing lens for an integrator. Illuminating light entering the entrance-side integrator lens is divided into luminous fluxes with plural optical axes, and then is made to enter the opposed exit-side integrator lens, and the respective luminous fluxes are diffused there, and then combined substantially concentrically by the condensing lens for an integrator and emitted to the condensing lens side.

SUMMARY OF THE INVENTION

A light source apparatus according to an embodiment of the present invention includes: a light source section that emits a luminous flux whose quantity of light is larger in a central region than in a peripheral region; a condensing optical system that condenses an incoming luminous flux; and a light distribution correction optical element arranged between the light source section and the condensing optical section, in which a central portion has a negative power that is more intense than that of a peripheral region.

An endoscope system according to another embodiment of the present invention includes the light source apparatus, and an endoscope including a light guide that guides light from the light source apparatus.

DETAILED DESCRIPTION OF THE PREFERRED EMBODIMENTS

<First Embodiment>

Figure 1:
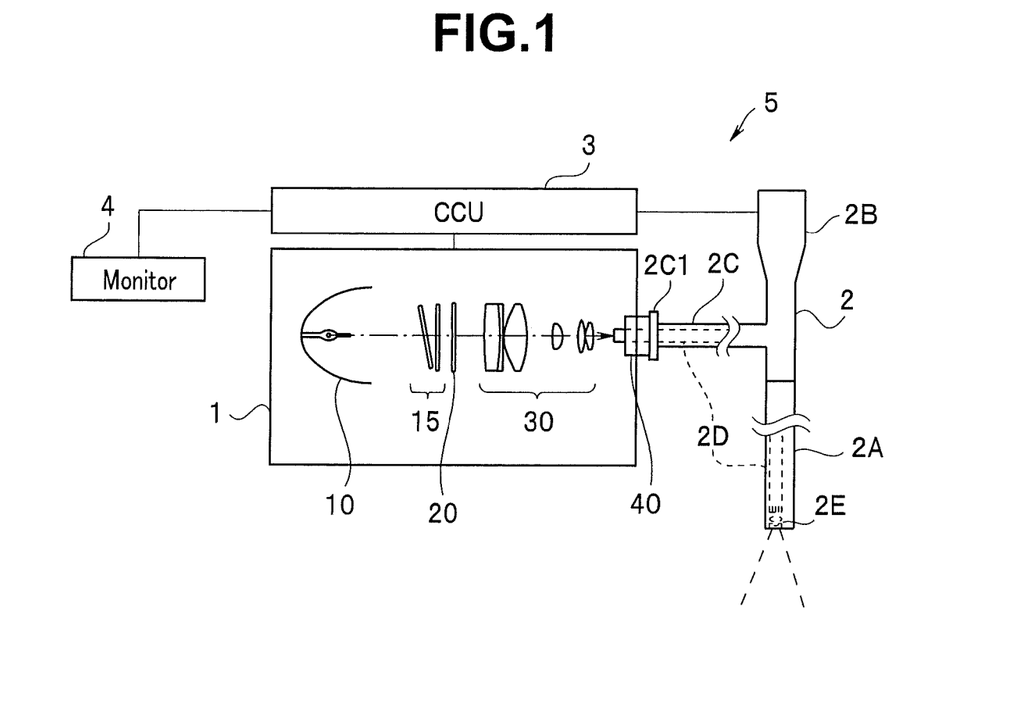
FIG. 1 is a diagram of a configuration of a light source apparatus according to a first embodiment.

As illustrated in FIG. 1, a light source apparatus 1 according to a first embodiment forms an endoscope system 5 jointly with, e.g., an endoscope 2, a CCU (camera control unit) 3 and a monitor 4. The endoscope 2 includes an operation section 2B arranged on a proximal end side of an elongated insertion portion 2A to be inserted into a body cavity, and a light guide cable 2C connected to a side portion of the operation section 2B.

A light guide connector 2C1 is arranged at an extended distal end portion of the light guide cable 2C, and the light guide connector 2C1 is connectable to a connector portion 40 of the light source apparatus 1. A light guide 2D is inserted through the light guide cable 2C.

Light generated by the light source apparatus 1 is guided to a distal end portion of the insertion portion 2A via the light guide 2D, and is emitted toward an object via an illumination optical system 2E. An image of the illuminated object is picked up by an image pickup device (not illustrated) such as a CCD, arranged at the distal end portion, and signals of the picked-up image are subjected to signal processing in the CCU 3, and then displayed on a screen of the monitor 4 as an endoscopic image.

Figure 2:
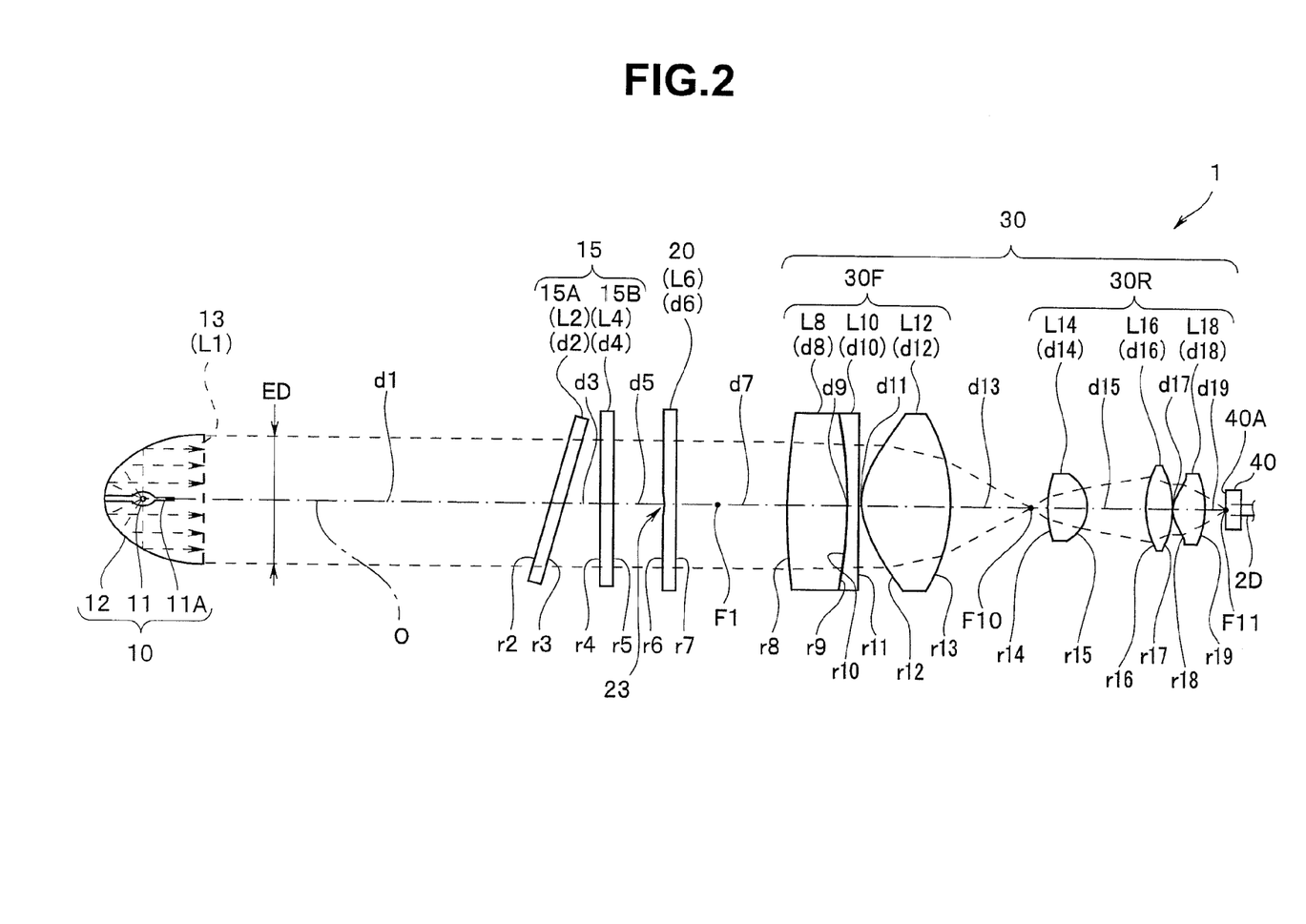
FIG. 2 is a diagram of a configuration of an optical system of the light source apparatus according to the first embodiment.

As illustrated in FIGS. 1 and 2, the light source apparatus 1 includes a light source section 10, a filter unit 15 and a light distribution correction optical element (hereinafter also referred to as "correction element") 20, which is a light distribution correction optical system, a condensing optical system 30 and a connector portion 40. The light source section 10 includes a light source 11 including a discharge lamp such as a xenon lamp or a metal halide lamp, and a reflector 12 having a parabolic shape. The light source 11 includes an electrode 11A having a small diameter in an optical path.

Figure 3A:
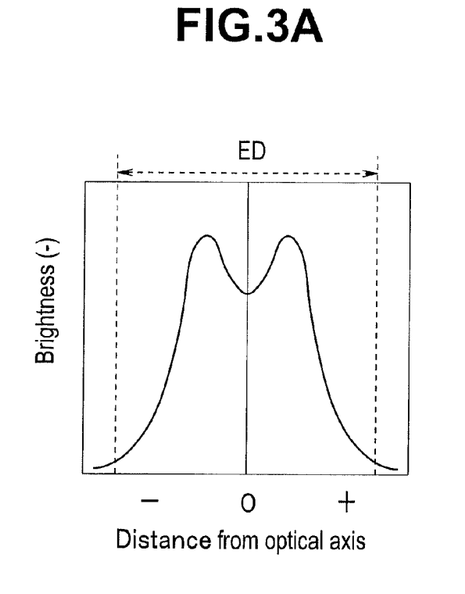
FIG. 3A is a diagram for illustrating an intensity distribution of a luminous flux emitted by a light source section.
Figure 3B:
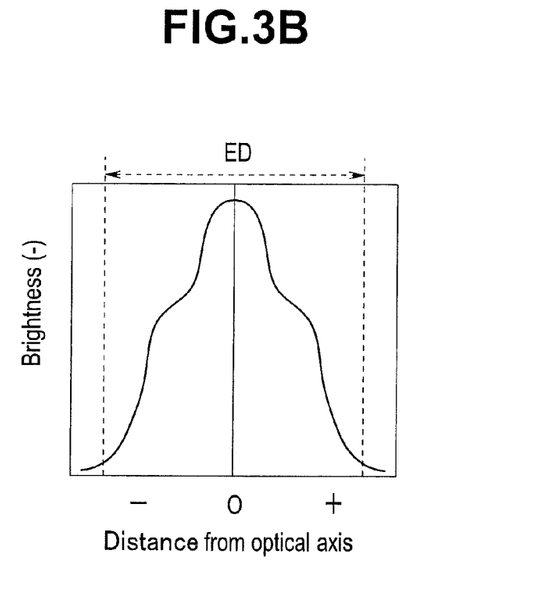
FIG. 3B is a diagram for illustrating an intensity distribution of a luminous flux emitted by a light source section.

Furthermore, as illustrated in FIG. 3A, with a light source section that causes a hollow defect, a quantity of emitted luminous flux is smaller in a region in the vicinity of an optical axis O, that is, a central region, than in a peripheral region. Meanwhile, as illustrated in FIG. 3B, with the light source section 10, a quantity of emitted luminous flux is larger in a central region than in a peripheral region. An effective luminous flux diameter (ED) indicated in each of FIGS. 3A and 3B is an outer diameter of a luminous flux having a quantity of light that is 95% of a luminous flux emitted by the light source section (hereinafter also simply referred to as "diameter").

Since the light source section 10 has the discharge electrode 11A having a small diameter and a valve and is arranged so as to emit a large quantity of luminous flux, the light source section 10 provides a luminous flux distribution in which a relative intensity is high in a center, such as, for example, a luminous flux distribution having a luminous flux density of no more than 80% within a diameter that is ±30% from a center of the effective luminous flux diameter (ED) relative to a luminous flux density in a center (on an optical axis). It should be noted that, e.g., a light emitting diode may be used as the light source, and the reflector 12 may not be provided as long as such light emitting diode is a light source apparatus that emits a luminous flux whose quantity of light is larger in a central region than in a peripheral region.

The filter unit 15 includes an ultraviolet cut filter 15A (L2) and an infrared cut filter 15B (L4). For example, the ultraviolet cut filter 15A is a filter that transmits visible light and blocks ultraviolet light, and the infrared cut filter 15B is a filter that transmits visible light and blocks infrared light.

Figure 4A:
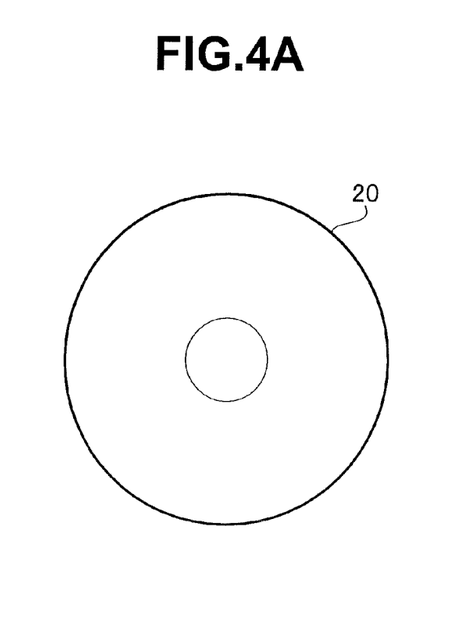
FIG. 4A is a front view of a light distribution correction optical element of the light source apparatus according to the first embodiment.
Figure 4B:
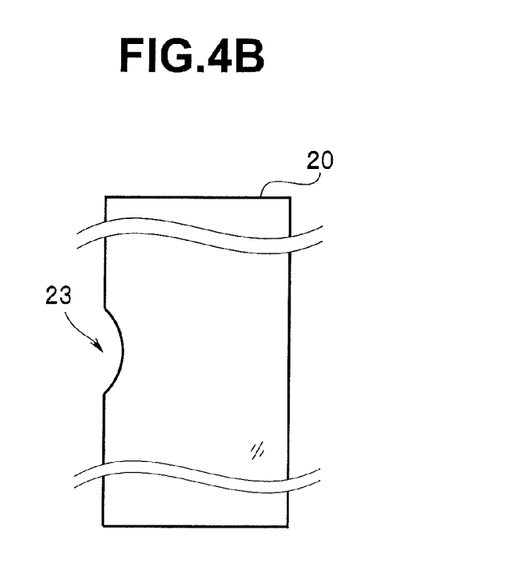
FIG. 4B is a cross-sectional view of the light distribution correction optical element of the light source apparatus according to the first embodiment.

As illustrated in FIGS. 4A and 4B, the correction element 20 (L6) is a single piece of glass having a substantially-flat plate shape. The correction element 20 includes a recess portion 23 formed at a central portion of a side thereof, whereby the central portion serves as a lens having a negative power. For example, as described later, a wall surface of the recess portion 23 is a spherical surface with a curvature radius of 40 mm and having a depth of 280 µm.

The central portion of the correction element 20 may have a conical shape or a shape of a Fresnel lens or a diffracting grating as long as the central portion forms a lens having a negative power. However, from the perspective of ease of manufacturing, a spherical shape is preferable. In other words, a correction element 20 obtained by forming a spherical recess portion at a center of one surface of a flat glass plate is easy to manufacture as well as being inexpensive.

The condensing optical system 30 includes a front lens group 30F and a rear lens group 30R. The front lens group 30F includes lenses L8, L10 and L12, and the rear lens group 30R includes lenses L14, L16 and L18. The condensing optical system 30 is what is called a relay optical system in which an incoming luminous flux is condensed by the front lens group 30F to a focal point F10, and then diffused and condensed again to a focal point F11 of the rear lens group 30R. In the condensing optical system 30, which is a relay optical system, a luminous flux has a small angle to an optical axis O between the front lens group 30F and the rear lens group 30R, and thus, it is suitable to provide, e.g., a color filter between the front lens group 30F and the rear lens group 30R. Also, in the condensing optical system 30, which is a relay optical system, an effective radius of the rear lens group 30R is smaller than an effective radius of the front lens group 30F, and thus, the condensing optical system 30 has a negative focal length. A negative focal length means that a position of a principal plane of the condensing optical system 30 is on the rear side relative to the rear-side focal point F11 of the rear lens group 30R.

Table 1 below indicates numerical data, etc., of optical members included in the light source apparatus 1. In the numerical data, r is a curvature radius of each surface, d is a thickness of each optical member or an air space between the respective optical members, n is an refractive index of each optical member for an e-line, ν is an Abbe number of each optical member for the e-line, and ER represents an effective radius. The unit of r, d and ER is mm.

TABLE 1

| | | | |
|---|---|---|---|
| r1 = ∞ | d1 = 69.6300 | | ER1 = 12.700 |
| r2 = ∞ | d2 = 3.0000 | n2 = 1.47310  ν2 = 66.02 | ER2 = 17.150 |
| r3 = ∞ | d3 = 7.2000 | | ER3 = 17.150 |
| r4 = ∞ | d4 = 3.0000 | n4 = 1.52600  ν4 = 65.90 | ER4 = 18.300 |
| r5 = ∞ | d5 = 10.4000 | | ER5 = 18.300 |
| r6 = *1 | d6 = 2.0000 | n6 = 1.47310  ν6 = 66.00 | ER6 = 19.000 |
| r7 = ∞ | d7 = 23.0000 | | ER7 = 19.000 |
| r8 = 210.9400 | d8 = 12.0000 | n8 = 1.51825  ν8 = 64.10 | ER8 = 18.500 |
| r9 = −84.7800 | d9 = 0.0100 | | ER9 = 19.000 |
| r10 = −87.7800 | d10 = 2.5000 | n10 = 1.76168 ν10 = 28.50 | ER10 = 18.700 |
| r11 = ∞ | d11 = 0.5000 | | ER11 = 18.700 |
| r12 = 16.7900 | d12 = 18.0000 | n12 = 1.52522 ν12 = 58.90 | ER12 = 19.000 |
| r13 = −37.0200 | d13 = 19.9400 | | ER13 = 19.000 |
| r14 = 21.7600 | d14 = 8.0000 | n14 = 1.52563 ν14 = 58.60 | ER14 = 6.800 |
| r15 = −5.8500 | d15 = 12.0000 | | ER15 = 7.000 |
| r16 = 20.0000 | d16 = 5.5000 | n16 = 1.69979 ν16 = 55.50 | ER16 = 9.000 |
| r17 = −20.0000 | d17 = 0.1000 | | ER17 = 9.000 |
| r18 = 7.5000 | d18 = 6.5000 | n18 = 1.52563 ν18 = 58.60 | ER18 = 7.300 |
| r19 = −19.5700 | d19 = 4.4200 | | ER19 = 7.500 |

The optical members of the light source apparatus 1 are configured as indicated below.

Effective luminous flux diameter (ED) of the light source section 10: 30 mm
Outer size (RD) of the correction element 20: 38 mm (Table 1: ER6×2)

Diameter (φ) of the central region of the correction element 20: 8 mm
Curvature radius (r6) of the central region of the correction element 20: 40 mm (Table 1=*1)
Curvature radius (r6A) of a peripheral region of the correction element 20: ∞(Table 1=*1)
Focal length of the central region of the correction element 20: fc=−84.6 mm
Focal length of the condensing optical system 30: f=−19.2 mm
Front-side focal position F1 of the condensing optical system 30: 103.6 mm from an output face (L1) of the light source section 10
Position to dispose the correction element 20: 93.2 mm from the output face (L1) of the light source section 10
Diameter (LD) of the light guide 2D to which the light source apparatus 1 is connected: 0.8 mm However, the "position to dispose the correction element 20" refers to a "position of a surface (r6) of the correction element 20 closest to the light source section 10".

Figure 5:
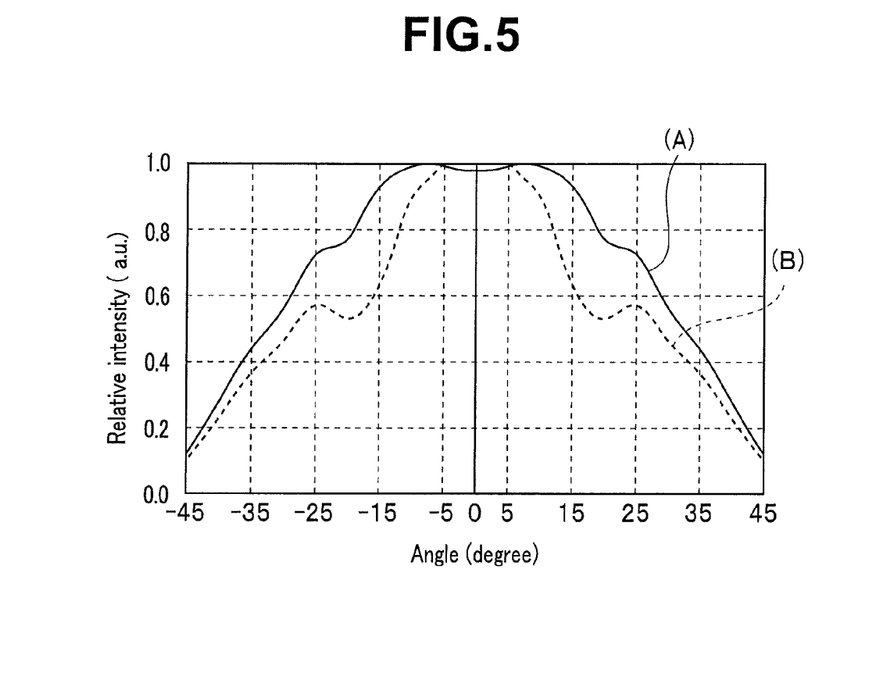
FIG. 5 is a diagram of light distribution characteristics of a light source apparatus.

Numerical results obtained by experiments are indicated below. FIG. 5 indicates light distribution characteristics in the connector portion 40 of the light source apparatus. FIG. 5A indicates a light distribution characteristic of the light source apparatus 1 having the above-described configuration, and FIG. 5B indicates a light distribution characteristic where no correction element was disposed. Although in the light distribution characteristics indicated in FIG. 5, light quantities are normalized to a maximum light quantity: a quantity of light in the case of (A), i.e., the light source apparatus 1, was 202.2 lumens (lm), while in the case of (B), i.e., where no correction element was provided, was 178.7 lumens.

Respective parameters in the light source apparatus 1 are indicated below.

An absolute value FR of a ratio between the focal length fc of the central region of the correction element 20 and the focal length f of the condensing optical system 30 is (FR=ABS (fc/f)=ABS (−84.6 mm/−19.2 mm)=4.4). Here, ABS(X) is an absolute value of X.

The position to dispose the correction element 20 is (93.2−103.6=−10.4 mm) if the position is indicated in relation to the front-side focal position F1 of the condensing optical system 30. Here, the value of the position being a minus figure means that the position is located on the light source section 10 side relative to the front-side focal position F1 of the condensing optical system 30 on the optical axis O. The position to dispose the correction element 20 is (SP=−10.4 mm/ABS (−19.2 mm)=−0.54) if the position is expressed by a ratio SP of the position relative to an absolute value of the focal length f of the condensing optical system 30.

The diameter φ of the central region of the correction element 20 is 8 mm, and the effective luminous flux diameter ED of a luminous flux emitted by the light source section 10 is 30 mm. Where the diameter φ of the central region of the correction element 20 is expressed by a value LR relative to the effective luminous flux diameter ED of a luminous flux emitted by the light source section 10, LR=8/30*100=27%.

Next, a light source apparatus having a basic structure that is the same as that of the light source apparatus 1 will be described in terms of, e.g., light distribution characteristics where a part of parameters of an optical system was changed.

<Focal Length (fc) of Center Portion of Correction Element>

Figure 6:
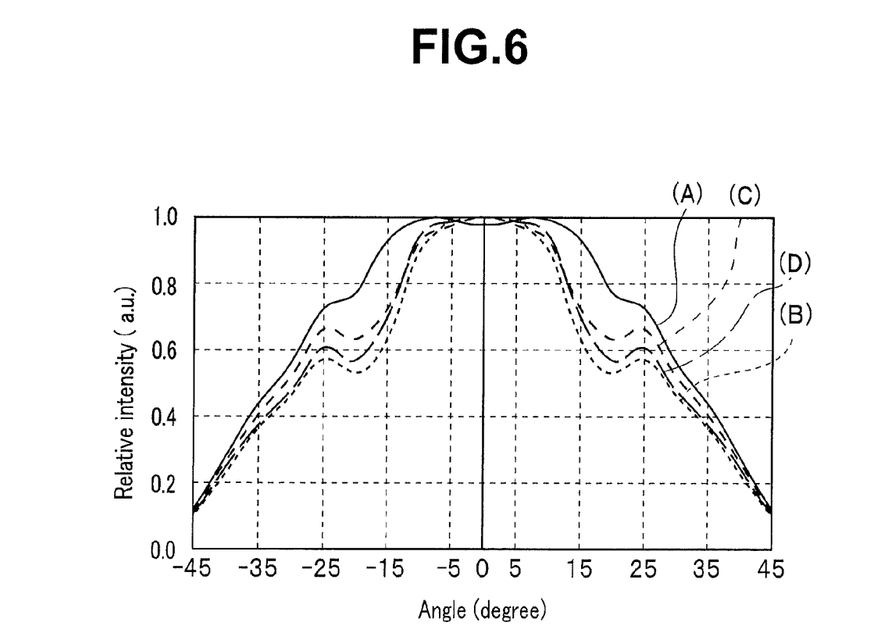
FIG. 6 is a diagram of light distribution characteristics of a light source apparatus.

FIG. 6 indicates a light distribution characteristic when a focal length fc of a central portion of a correction element 20 is (C) −42.3 mm and (D) −105.7 mm if φ=8 mm. In FIGS. 6, (A) and (B) indicate a light distribution characteristic when the focal length fc of the central portion of the correction element 20 is (A) −84.6 mm, and (B) where no correction element 20 was provided as in FIG. 5.

An absolute value FR of a ratio between the focal length fc of the central region of the correction element 20 and a focal length f of a condensing optical system 30 is (A) FR=4.4, (C) FR=2.2 and (D) FR=5.5.

<Diameter (φ) of Central Region of Correction Element>

Figure 7:
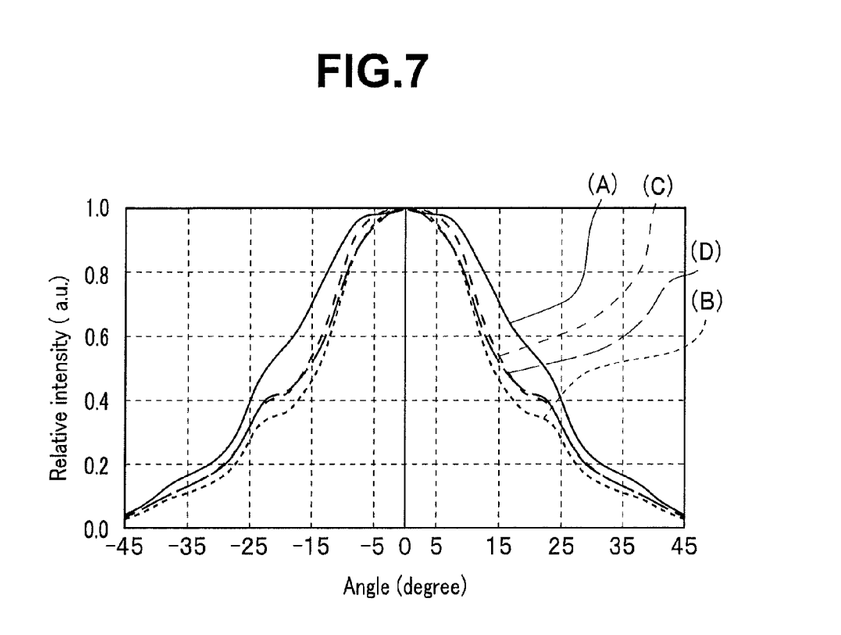
FIG. 7 is a diagram of light distribution characteristics of a light source apparatus.

FIG. 7 indicates light distribution characteristics where a diameter φ of the central region of the correction element 20 and the focal length fc of the central region of the correction element 20 were changed. In FIG. 7, (A) indicates a case where φ=8 mm and fc=−42.3 mm, (C) indicates a case where φ=6.4 mm and fc=−105.7 mm, and (D) indicates a case where φ=5.6 mm and fc=−42.3 mm, and (B) indicates a case where no correction element 20 was disposed.

Where the diameter φ of the central region of the correction element 20 is expressed by a value LR relative to an effective luminous flux diameter ED of a luminous flux emitted by a light source section 10, (A) LR=27%, (C) LR=21%, and (D) LR=19%.

<Position to Dispose Correction Element>

Figure 8:
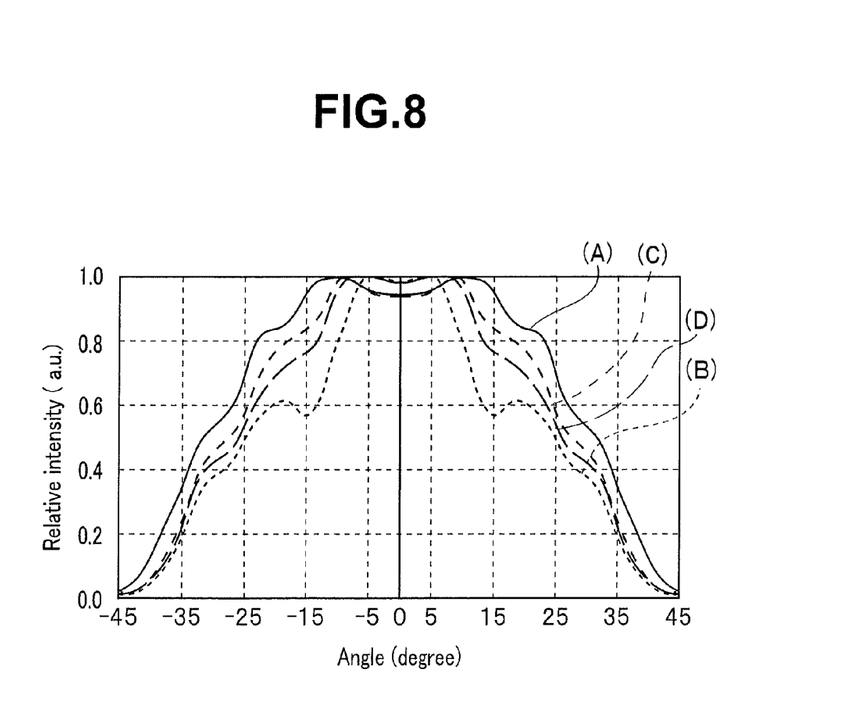
FIG. 8 is a diagram of light distribution characteristics of a light source apparatus.

FIG. 8 indicates light distribution characteristics where the position to dispose the correction element 20 was changed when fc=−84.6 mm. The position is a position (A) −10.1 mm, (C) +6 mm and (D) −16.9 mm from a front-side focal position F1 of the condensing optical system 30, and (B) indicates a case where no correction element 20 was disposed.

Where the position is expressed by a ratio SP of the position relative to the focal length f of the condensing optical system 30, (A) SP=−0.54, (C) SP=+0.31, and (D) SP=−0.88.

<Diameter (LD) of Light Guide 2D to which Light Source Apparatus is Connected>

Table 2 indicates quantities of condensed light where a diameter (LD) of a light guide (LG) 2C to which the light source apparatus 1 is connected is varied (unit: lumens).

TABLE 2

| LG diameter φ (mm) | 0.8 | 1.5 | 2.6 | 3.4 | 4.5 |
|---|---|---|---|---|---|
| Correction element provided | 202 | 674 | 1248 | 1415 | 1520 |
| No correction element provided | 179 | 661 | 1315 | 1444 | 1516 |

In other words, conditions of the correction element 20 for providing a light source apparatus in which a light distribution characteristic and a quantity of condensed light are well balanced are indicated below:
(Expression 1: Condition 1) 2.2<ABS (fc/f)<5.5, preferably,
(Expression 2: Condition 2) 3.0<ABS (fc/f)<5.0

(Expression 1) and (Expression 2) specify the absolute value FR of the ratio between the focal length fc of the central region of the correction element 20 and the focal length f of the condensing optical system 30. Although in FIG. 6, three cases of (A) FR=4.4, (C) FR=2.2 and (D) FR=5.5 are indicated, as a result of a further detailed study, there was an improvement in the light distribution characteristic of the light source apparatus where (Expression 1) was satisfied. For example, in the case of (B) where no correction element 20 was provided, a light intensity of a narrow angle component with an angel of 15 degrees (hereinafter referred to as "LM15") is 60% of a maximum light intensity (hereinafter referred to as "LM"); however, where (expression 1) was satisfied, the light intensity was improved to 80% or more. Furthermore, where (Expression 2) was satisfied, there was a further improvement, for example, LM15 was improved to be 90% or more of the LM.

(Condition 3) A correction element is disposed at a position $(-0.8 \times ABS(f))$ to $(+0.3 \times ABS(f))$ from of a front-side focal position of a condensing optical system.

(Condition 3) specifies the ratio SP of the position to dispose the correction element 20, relative to the focal length f of the condensing optical system 30. Although FIG. 8 indicates three cases, (A) SP=−0.54, (B) SP=+0.31 and (C) SP=−0.88, as a result of a further detailed study, where (Condition 3) was satisfied, there was an improvement in the light distribution characteristic of the light source apparatus. For example, in the case of (B) where no correction element 20 was disposed, the LM15 was 50% of the LM; however, where (Condition 3) was satisfied, the LM15 was improved to be 60% or more of the LM.

(Condition 4) A diameter of a central region of the correction element is 15% to 50%, preferably, (Condition 5) 20% to 30%, of a diameter of an effective luminous flux of a luminous flux emitted by a light source section.

(Condition 4) and (Condition 5) specify the value LR of the diameter (φ) of the central region of the correction element 20 relative to the effective luminous flux diameter ED of a luminous flux emitted by the light source section 10. FIG. 8 indicates three cases, (A) LR=27%, (C) LR=21% and (D) LR=19%; however, as a result of a further detailed study, where (Condition 4) was satisfied, there was an improvement in the light distribution characteristic of the light source apparatus. For example, in the case of (B) where no correction element 20 was disposed, the LM15 was 55% of the LM; however, where (Condition 4) was satisfied, the LM15 was improved to be 70% or more of the LM. Furthermore, where (Condition 5) was satisfied, there was a further improvement, for example, the LM15 was improved to be 80% or more of the LM.

The above measurements were made using a light source section 10 that provides a luminous flux distribution in which a relative intensity is high in a center, such as a luminous flux distribution having a luminous flux density of no more than 80% within a diameter that is ±30% from a center of an effective luminous flux diameter (ED) relative to a luminous flux density in a center (on an optical axis). However, as a result of measurements made with specifications of the light source section varied, it has been confirmed that Conditions 1 to 5 are effective as long as a light source section that emits a luminous flux whose quantity of light is larger in a central region than in a peripheral region, regardless of the degree of the largeness.

An effect of light distribution correction made by the above-described light distribution correction optical element can be obtained by increasing the power of the central portion (i.e., decreasing the focal length) or providing the light distribution correction optical element at a position closer to the light source; however, such effect has a trade-off relationship with the light condensing performance. In a range in which the above conditions are satisfied, a wide light distribution can be provided while the light condensing capability is ensured.

Alternatively, a condensing optical system with no light distribution correction optical element inserted is made to have a light condensing characteristic of somewhat excessively collecting light, to reduce a difference between a position where a luminous flux in a central portion is condensed and a position where a luminous flux in a peripheral portion is condensed when a light distribution correction element is inserted, enabling the efficiency to be ensured.

As described above, the light source apparatus 1 has a characteristic of a wide light distribution. Also, lenses in an integrator portion of a known light source apparatus each have a complicated shape, and required to have heat resistance, and thus, it is necessary to use a plurality of expensive glass lenses, and precise alignment of the lenses is required. Furthermore, it is not easy to reduce a size of a light source apparatus including an integrator portion. Meanwhile, in the light source apparatus 1, the correction element 20 includes one lens member, enabling reduction in size and cost.

<Second Embodiment>

Next, a light source apparatus 1A according to a second embodiment will be described. The light source apparatus 1A according to the present embodiment is similar to the light source apparatus 1 according to the first embodiment, and thus, components that are the same as those of the first embodiment are provided with reference numerals that are the same as those of the first embodiment and description thereof is omitted.

Figure 9:
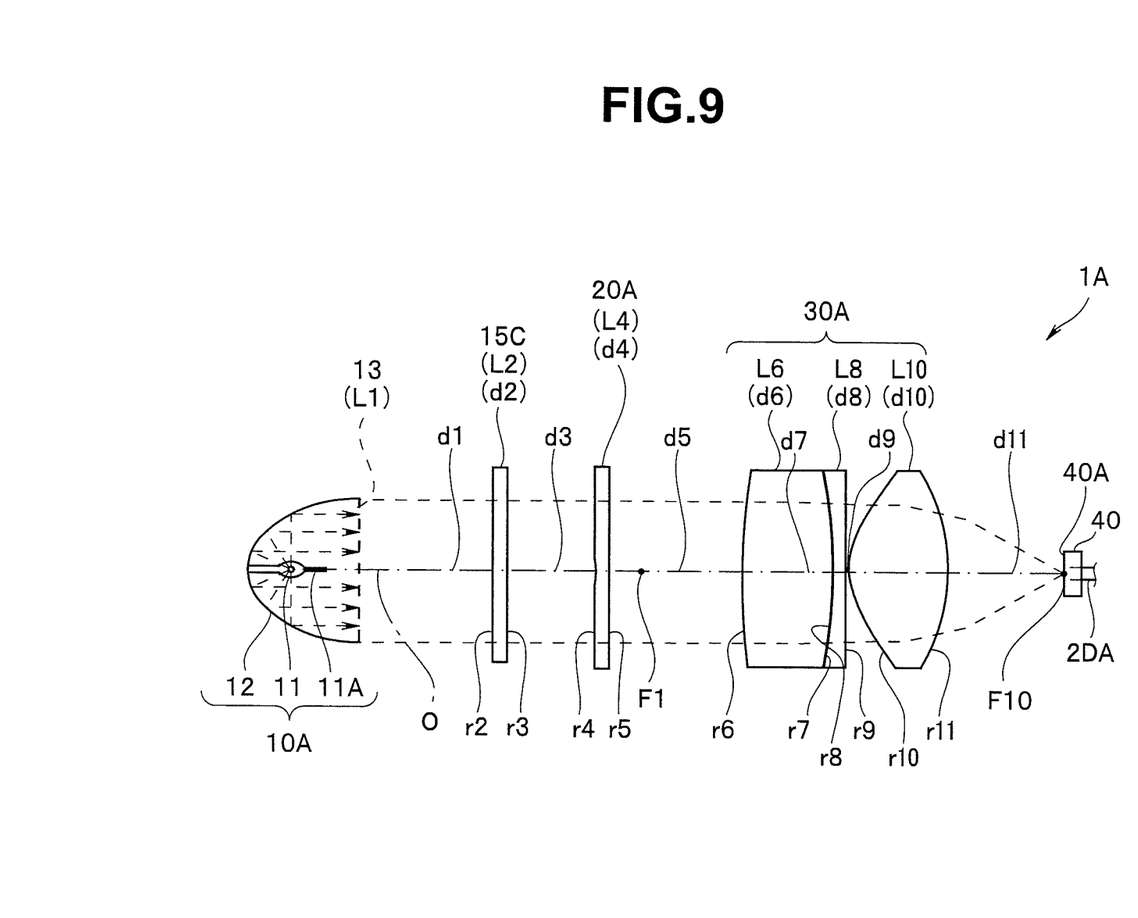
FIG. 9 is a diagram of a configuration of an optical system of a light source apparatus according to a second embodiment.

FIG. 9 illustrates a configuration of an optical system in the light source apparatus 1A. A condensing optical system 30A in the light source apparatus 1 includes lenses L6, L8 and L10. In other words, the condensing optical system 30A has a simple structure compared to the condensing optical system 30, which is a relay optical system, and thus, can be downsized. Furthermore, the light source apparatus 1 includes one infrared/ultraviolet cut filter 15C as a filter.

Table 3 below indicates numerical data, etc., of optical members included in the light source apparatus 1A.

TABLE 3

| | | | | |
|---|---|---|---|---|
| r1 = ∞ | d1 = 20.0000 | | | ER1 = 12.700 |
| r2 = ∞ | d2 = 3.0000 | n2 = 1.52600 | v2 = 65.90 | ER2 = 18.300 |
| r3 = ∞ | d3 = 13.4000 | | | ER3 = 18.300 |
| r4 = *2 | d4 = 2.0000 | n4 = 1.47310 | v4 = 66.00 | ER4 = 19.000 |
| r5 = ∞ | d5 = 20.0000 | | | ER5 = 19.000 |
| r6 = 210.9400 | d6 = 12.0000 | n6 = 1.51825 | v6 = 64.10 | ER6 = 18.500 |
| r7 = −84.7800 | d7 = 0.0100 | | | ER7 = 19.000 |
| r8 = −84.7800 | d8 = 2.5000 | n8 = 1.76163 | v8 = 27.50 | ER8 = 18.700 |
| r9 = ∞ | d9 = 0.5000 | | | ER9 = 18.700 |
| r10 = 16.7900 | d10 = 18.0000 | n10 = 1.59143 | v10 = 61.20 | ER10 = 19.000 |
| r11 = −37.0200 | d11 = 15.6000 | | | ER11 = 19.000 |

The optical members of the light source apparatus 1A are configured as indicated below.

Effective luminous flux diameter (ED) of the light source section 10A: 30 mm

Outer size (RD) of a correction element 20A: 38 mm (Table 2=ER4×2)

Diameter (φ) of a central region of the correction element 20A: 8 mm r (r6) of the central region of the correction element 20A: −33.1 mm (Table 2: *2)

r (r6A) of a peripheral region of the correction element 20A: ∞(Table 2: *2)

Focal length of the central region of the correction element 20A: fc=−70.0 mm

Focal length of the condensing optical system 30A: f=22.9 mm

Front-side focal position F1 of the condensing optical system 30A: 47.7 mm from an output face (L1) of a light source section 10

Position to dispose the correction element 20A: 36.4 mm from the output face (L1) of the output light source section 10

Figure 10:
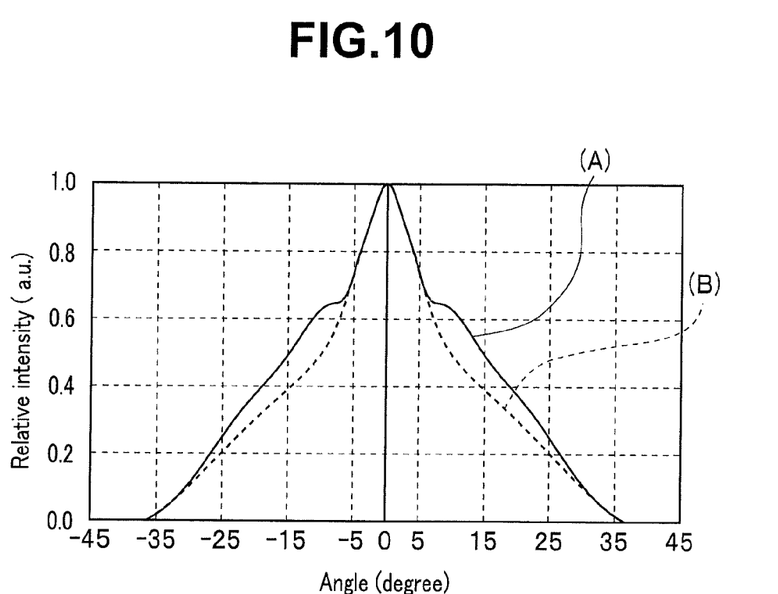
FIG. 10 is a diagram of light distribution characteristics of light source apparatuses.

Diameter (LD) of a light guide 2DA to which the light source apparatus 1A is connected: 2.2 mm FIG. 10 indicates light distribution characteristics in a connector portion 40 of the light source apparatus 1A. In FIG. 10, (A) indicates a light distribution characteristic of the light source apparatus 1A having the above-described configuration, and (B) indicates a light distribution characteristic where no correction element 20A was disposed.

In the light distribution characteristics indicated in FIG. 10, light quantities are normalized to a maximum light quantity: a quantity of light in the case of (A), e.g., the light source apparatus 1A, was 772 lumens, while a quantity of light in the case of (B), i.e., where no correction element was provided, was 753 lumens.

Respective parameters in the light source apparatus 1A are indicated below.

Absolute value of a ratio between the focal length fc of the central region of the correction element 20A and the focal length f of the condensing optical system 30: FR=ABS (−70/22.9)=3.1

Value of a diameter φ of the central region of the correction element 20A relative to the effective luminous flux diameter ED of a luminous flux emitted by the light source section 10: LR=8/30*100=27%

Ratio of the position to dispose the correction element 20A, relative to the focal length f of the condensing optical system 30A: SP=(36.4−47.7)/22.9=−0.49

<Diameter (LD) of Light Guide 2D to Which Light Source Apparatus 1A is Connected (LD)>

Table 4 indicates quantities of condensed light where the diameter (LD) of the light guide (LG) 2C to which the light source apparatus 1A is connected is varied (unit: lumens).

TABLE 4

| LG diameter φ (mm) | 2.2 | 3.0 | 3.8 | 4.6 |
|---|---|---|---|---|
| Correction element provided | 772 | 1072 | 1288 | 1450 |
| No correction element provided | 753 | 1083 | 1327 | 1500 |

As described above, the light source apparatus 1A satisfies (Condition 2), (Condition 3) and (Condition 4), which have already been described. Furthermore, as illustrated in FIG. 9, the light source apparatus 1A has a characteristic of a wide light distribution, and light condensing performance thereof does not easily deteriorate. Furthermore, it has otherwise been confirmed that (Condition 1) to (Condition 5) are effective also in the light source apparatus 1A.

The light source apparatus 1A has effects the light source apparatus 1 according to the first embodiment has, and in addition, has a simple structure and a small size.

<Third Embodiment>

Next, a light source apparatus 1B according to a third embodiment will be described. The light source apparatus 1B according to the present embodiment is similar to the light source apparatus 1 according to the first embodiment and the like, and thus, components that are the same as those of the first embodiment and the like are provided with reference numerals that are the same as those of the first embodiment and the like, and a description thereof will be omitted.

Figure 11:
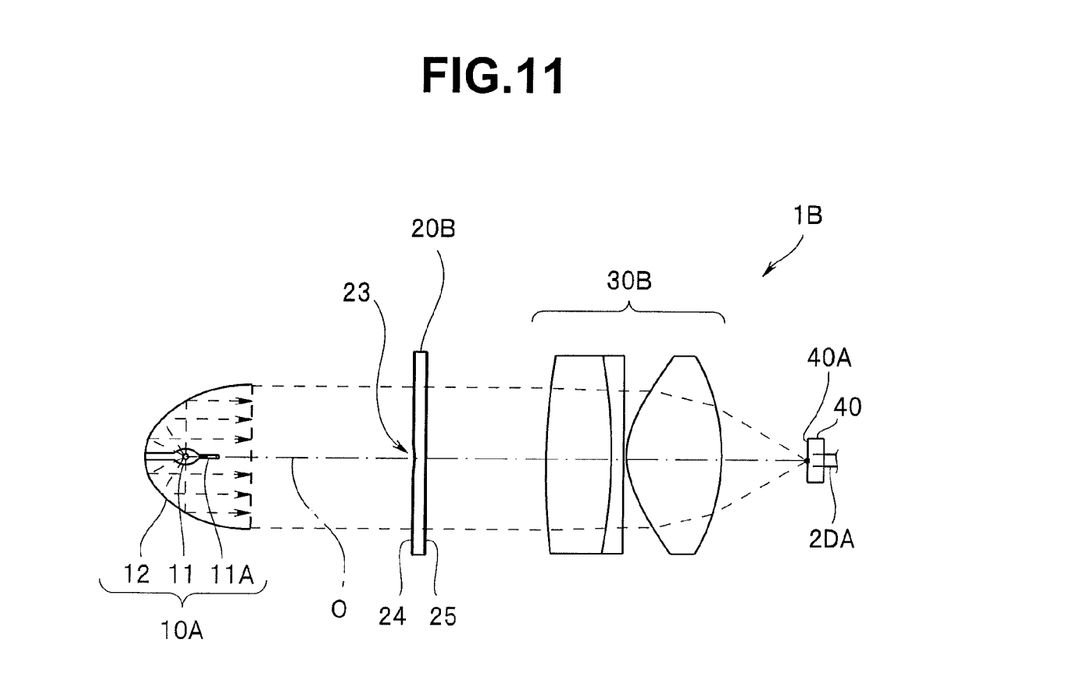
FIG. 11 is a diagram of a configuration of an optical system of a light source apparatus according to a third embodiment.

As illustrated in FIG. 11, the light source apparatus 1B includes a correction element 20B including an ultraviolet cut film 24 formed on one surface thereof, and an infrared cut film 25 formed on another surface thereof. In other words, the correction element 20B is a substantial flat plate including one piece of glass, but has an ultraviolet cut filter function and an infrared cut filter function in addition to a light distribution correction optical function. Alternatively, in the correction element 20B, a stack of an ultraviolet cut film and an infrared cut film may be formed, or only either one of the ultraviolet cut film 24 and the infrared cut film 25 may be formed.

For each of the ultraviolet cut film 24 and the infrared cut film 25, a known film may be used. A shape of a center portion of the correction element 20B provides a lens having a negative power, but a recess portion 23 has a small depth, and a wall surface of the recess portion 23 is a spherical surface. Thus, even if, e.g., a vacuum film forming method, such as a known sputtering method, or a solution applying method is used as a method for forming the ultraviolet cut film 24 and the infrared cut film 25, uniform films with no unevenness can be formed on the correction element 20B. The light source apparatus 1B has effects the light source apparatuses 1 and 1A have, and in addition, has a simple configuration and thus, can easily be downsized.

As described above, the present invention is not limited to the above-described embodiments, and various alternations, modifications and the like are possible as long as such alternations, modifications and the like do not change the spirit of the present invention.

What is claimed is:

1. A light source apparatus comprising:
    a light source section that emits a luminous flux whose quantity of light is larger in a central region than in a peripheral region;
    a condensing optical system that condenses an incoming luminous flux;
    a light distribution correction optical element positioned between the light source section and the condensing optical system, the light distribution correction optical element including a discrete central portion separated from a peripheral portion by a well-defined boundary, the discrete central portion having a constant negative power higher than that of the peripheral portion of the light distribution correction optical element; and
    a connector section capable of being detachably connected with a light guide that guides the luminous flux condensed by the condensing optical system;
    wherein the light source apparatus satisfies the expression 2.2<|fc/f|<5.5, where fc is the focal length of the discrete central portion of the light distribution correction optical element, and f is a focal length of the condensing optical system.

2. The light source apparatus according to claim 1, wherein the light source apparatus satisfies the expression:

3.0<ABS (fc/f)<5.0.

3. The light source apparatus according to claim 2, wherein the light distribution correction optical element is arranged at a position (−0.8×ABS(f)) to (+0.3×ABS(f)) from a front-side focal position of the condensing optical system.

4. The light source apparatus according to claim 3, wherein a diameter of the central region of the light distribution correction optical element is 15% to 50% of a diameter of an effective luminous flux of the luminous flux emitted by the light source section.

5. The light source apparatus according to claim 4, wherein the diameter of the central region of the light distribution correction optical element is 20% to 30% of the diameter of the effective luminous flux of the luminous flux emitted by the light source section.

6. The light source apparatus according to claim 5, wherein at least one of an ultraviolet cut film and an infrared cut film is formed on at least one surface of the light distribution correction optical element.

7. An endoscope system comprising:
- a light source apparatus including a light source section that emits a luminous flux whose quantity of light is larger in a central region than in a peripheral region, a condensing optical system that condenses an incoming luminous flux, and a light distribution correction optical element positioned between the light source section and the condensing optical system, the light distribution correction optical element including a discrete central portion separated from a peripheral portion by a well-defined boundary, the discrete central portion having a constant negative power higher than that of the peripheral portion of the light distribution correction optical element, and a connector section detachably connected with a light guide that guides the luminous flux condensed by the condensing optical system; and
- an endoscope including a light guide that guides light from the light source apparatus;
- wherein the light source apparatus satisfies the expression $2.2<|fc/f|<5.5$, where fc is the focal length of the discrete central portion of the light distribution correction optical element, and f is a focal length of the condensing optical system.

* * * * *